United States Patent [19]

Wagner et al.

[11] Patent Number: 4,669,302

[45] Date of Patent: Jun. 2, 1987

[54] DEFLECTION AND TOPOGRAPHY ASSESSMENT MECHANISM ANTHROPOMORPHICALLY NATURAL

[75] Inventors: Robert F. Wagner, Lombard; Jack L. Lewis, Evanston, both of Ill.

[73] Assignee: Sealy, Incorporated, Chicago, Ill.

[21] Appl. No.: 726,485

[22] Filed: Apr. 24, 1985

[51] Int. Cl.[4] .......................................... G01N 19/00
[52] U.S. Cl. ........................................ 73/172; 73/818
[58] Field of Search .................. 73/172, 132 R, 161, 73/818

[56] References Cited

U.S. PATENT DOCUMENTS

| | | | |
|---|---|---|---|
| 3,147,617 | 9/1964 | Kaptur, Jr. et al. | 73/172 |
| 3,413,849 | 12/1968 | Janapol | 73/161 |
| 3,762,069 | 10/1973 | Culver. | |
| 3,962,801 | 6/1976 | Gonzalez. | |

FOREIGN PATENT DOCUMENTS

| | | |
|---|---|---|
| 2542268 | 4/1976 | Fed. Rep. of Germany. |
| 2922619 | 12/1980 | Fed. Rep. of Germany. |
| 2123609 | 9/1972 | France. |
| 2358716 | 2/1978 | France. |
| 986093 | 3/1965 | United Kingdom. |

OTHER PUBLICATIONS

"Sealy Man" materials prepared by Sealy, Inc. circa 1973, 1975.

Primary Examiner—Jerry W. Myracle
Attorney, Agent, or Firm—Willian Brinks Olds Hofer Gilson & Lione

[57] ABSTRACT

An apparatus particularly suited for measuring the shape or contour of a surface under load, such as a mattress, is comprised of a humanoid having body limb extremities which are movable in a manner similar to the movement of comparable human extremities. Sensors are placed at joints, such as the knees and hips, to measure the amount of relative movement, i.e. deflection, that occurs at these joints when the humanoid is placed upon a mattress surface. The sensors provide an indication of the shape or contour of the mattress surface by correlation of the relative movement that occurs at these joints caused by the underlying mattress shape. In its preferred form, a movable frame is provided to raise and lower the humanoid in relation to the mattress surface to be tested. A "spine" is also advantageously provided with associated sensors to measure deflection, and thus surface contour, in the lower torso/abdominal region.

11 Claims, 13 Drawing Figures

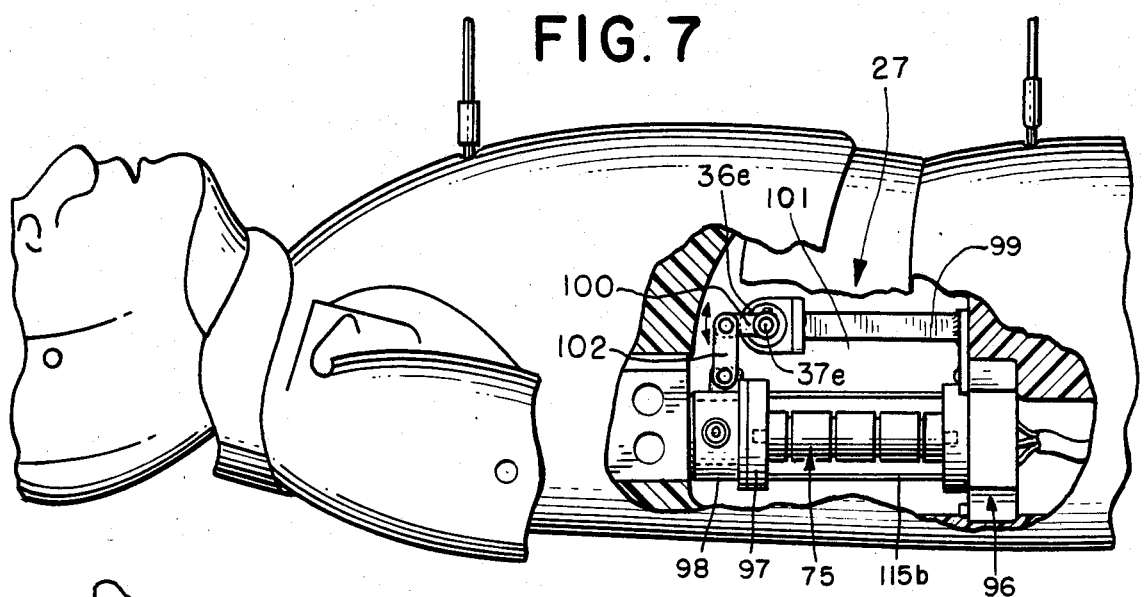
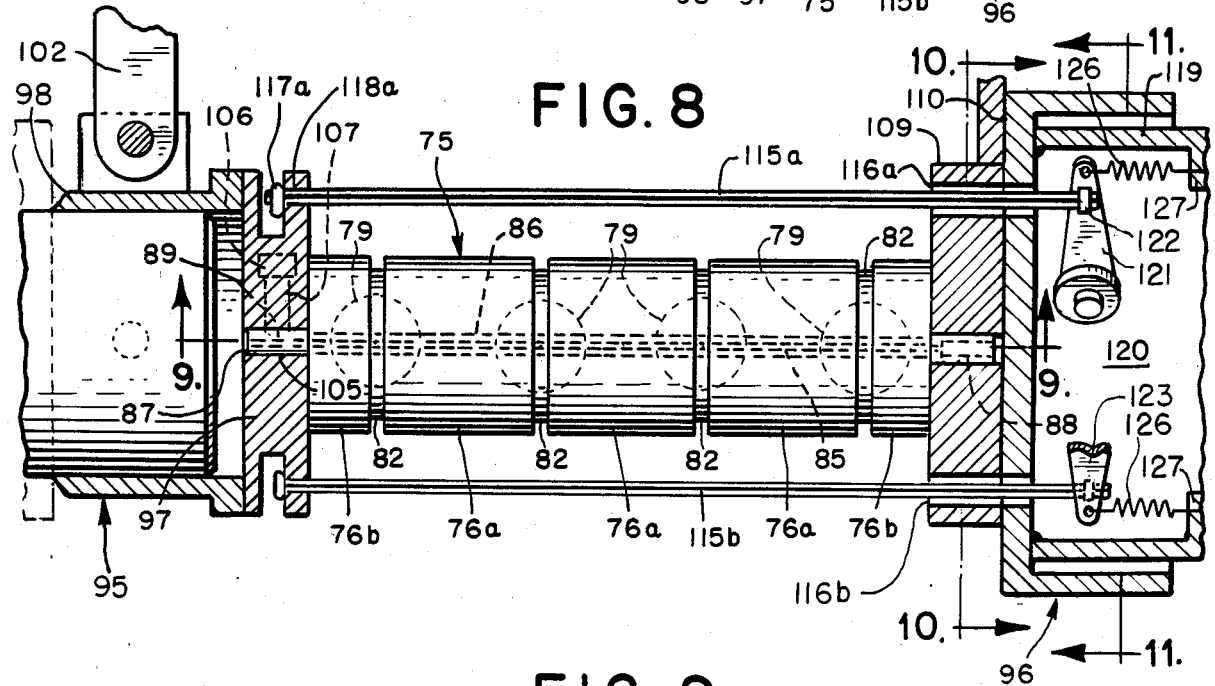
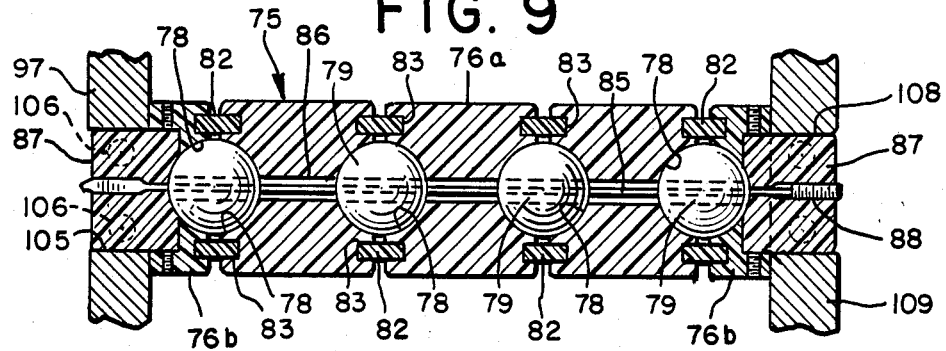

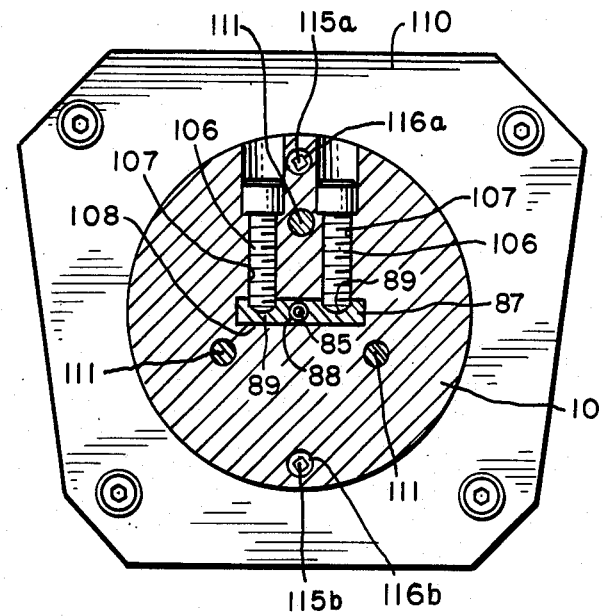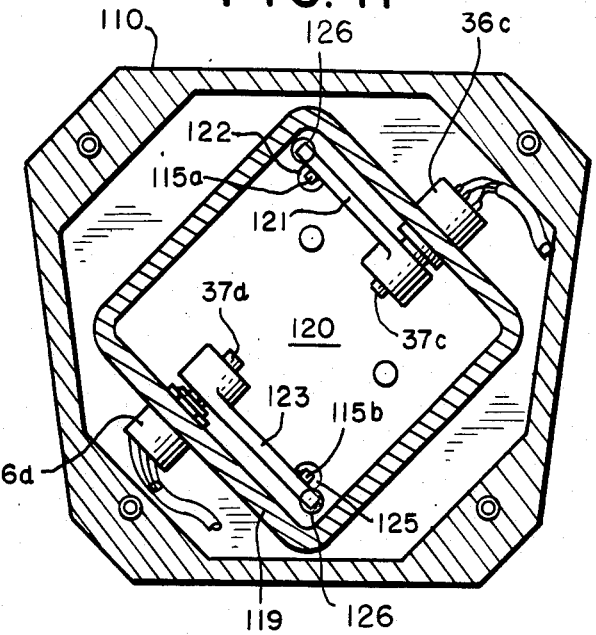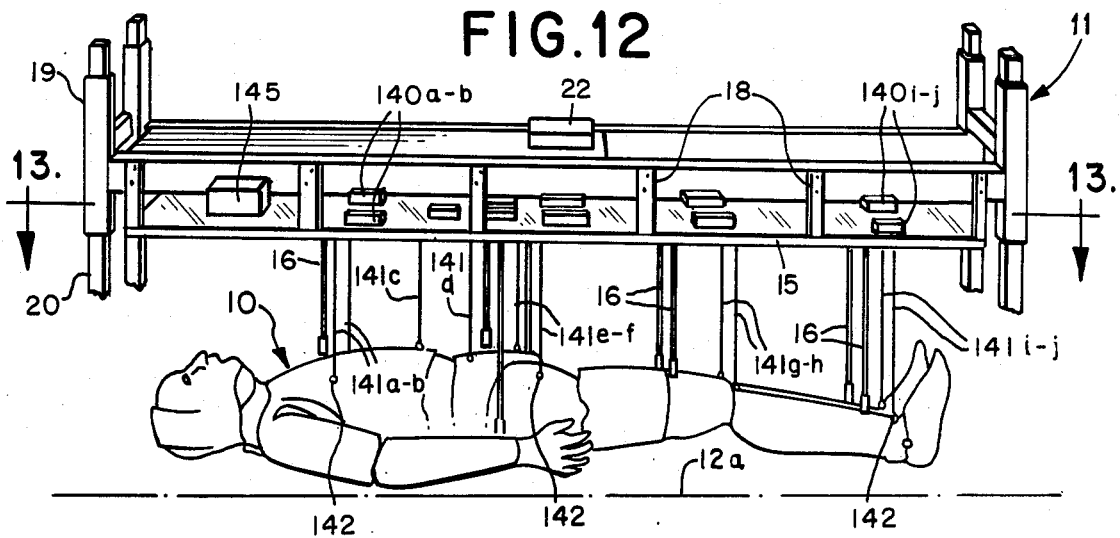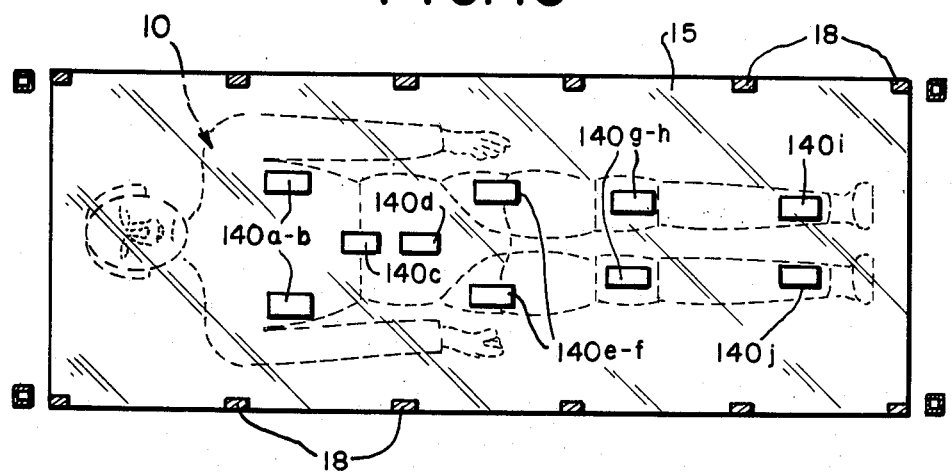

DEFLECTION AND TOPOGRAPHY ASSESSMENT MECHANISM ANTHROPOMORPHICALLY NATURAL

FIELD OF THE INVENTION

This invention is related to an apparatus for measuring the shape or contour of a surface in relation to the form of the human body. That is, the invention yields an indication of surface contour as reflected by position changes of bodily parts of a human-shaped figure placed on the surface. In particular, the invention relates to an apparatus useful in measuring the shape or contour of a mattress surface under load from such a human-shaped figure.

BACKGROUND OF THE INVENTION

The present invention has its genesis in the field of mattress construction. In general, mattresses have an innerspring assembly composed of a plurality of coil springs which are arranged in a pattern within a border wire framework, with the coils and framework joined together in an intergral whole. Typically, multiple layers of insulative and other sheet material overlie the innerspring assembly, culminating in an outer covering layer of soft fabric.

One objective in designing a mattress is to optimize the distribution of pressure over the human body in a "deformed" profile, e.g., sleep position, while also providing satisfactory firmness. This objective has been quantified in one instance as an "idealized support profile" or model.

Measuring whether a mattress matches such an idealized model, or for that matter, matches whatever contour or shape is ultimately desired for the mattress when under load by a human being, has been a relatively inexact science to date. For example, one known way to measure the shape or contour of the mattress is to test it under load at various discrete points, typically along a line extending parallel to the longitudinal axis of the mattress. These individual data points can then be plotted to give an indication of the mattress "firmness" along that line. This method of measuring mattress contour is deficient in that the information obtained is only of a relatively small discrete area under load, and does not reflect shape or contour of the mattress under a wide area load, such as the human body. The measurement also takes an undesirable length of time to obtain, in light of the fact that a plurality of point measurements must be taken, typically one at a time.

Another known way of obtaining an indication of "feel" of a mattress is to have a group of individuals lie on the mattress surface one after another, and then compile their various verbal impressions of how the mattress "felt." While this "measurement" of the shape and surface of a mattress is plainly related to the configuration of the mattress under the wide area load of the human body, it obviously lacks objective detail, consistency and repeatability.

SUMMARY OF THE INVENTION

It is a principal objective of this invention to provide an apparatus for use in measuring the shape or contour of a surface as reflected in positional changes of a human-shaped figure. More particularly, it is a specific objective of this invention to provide such an apparatus which can rapidly, objectively and repeatably indicate the shape or contour of a mattress surface under the deformed profile load of an object with human shape and mass distribution.

These objectives have been met in the present invention which is comprised of a humanoid having body limb extremities similar in size and shape to those of the human body. One or more of those extremities is made to be movable in a manner similar to the movement of a comparable human extremity, at least in one plane of motion. For example, a present embodiment of the invention provides for movement of the humanoid leg at the knee joint and the hip joint such that the leg can bend or rotate at these joints in a plane parallel to a plane bisecting the humanoid figure, i.e., in a vertical plane if the humanoid is lying horizontally on its back.

The humanoid is further constructed in a manner which at least grossly reproduces the size and shape of the human body, including its relative hardness or softness in certain areas, as well as its areas of higher or lower mass (i.e., its weight is distributed in proportion to the male human body).

Positional sensing devices are located at selected points on the humanoid figure. The sensing devices detect the amount of relative movement, or deflection, which that area of the figure undergoes when placed in contact with a surface to be measured. For example, a present embodiment of the invention locates position transducers in the form of rotary potentiometers at the hip and knee joints to indicate the deflection in these areas caused by the surface configuration. A device reproducing a portion of the human spine is also advantageously provided, and has an associated positional sensing mechanism for indicating deflection in the area of the lower back/abdomen.

This present embodiment of the invention further includes a movable support assembly from which the humanoid is horizontally suspended, such that it can be readily lowered onto and raised from a surface to be measured. The movable support is in the form of a motor driven frame which moves up and down a set of supporting legs, with the humanoid suspended below the frame.

In use, the humanoid is lowered by the support mechanism into contact with a surface which is to have its shape or contour measured, such as a mattress. The humanoid is allowed to rest with its full weight supported by the mattress surface. Movements of the legs, hips and lower back/abdomen caused by the mattress surface contour are detected by the position transducers in the form of voltage changes in the transducer circuit. These voltage changes can then be translated into a measurement of the contour of the surface as reflected by the relative changes in position of the humanoid's joints and "spine."

As applied to mattresses, the invention provides a means for measurement of mattress contour under a wide area load of a human figure. This actual mattress contour can then be compared to the "idealized support profile" for example, to determine how closely the mattress matches such a desired configuration.

It will also be recognized that, while measurement of a surface contour is a principal objective of this invention, measurement of the effect of a surface contour on the humanoid is also of separate significance. That is, changes in position of the humanoid's bodily parts caused by the surface can be related to likely human body responses, e.g., deflection in the abdominal area resulting in low back pain. This invention can thus be utilized in measuring a surface contour, as well as estimating its physiological impact on the human body.

The features and advantages of this invention will be more particularly understood with reference to the detailed description and drawings which follow, in which:

BRIEF DESCRIPTION OF THE DRAWINGS

FIG. 7 is an elevational view of the torso, partly broken away to detail placement of the spine mechanism;

FIG. 8 shows the spine mechanism removed from the torso;

FIG. 9 is a sectional view taken along line 9—9 of FIG. 8 detailing the spine stack or column;

FIG. 10 is a sectional view taken along line 10—10 of FIG. 8;

FIG. 11 is a sectional view taken along line 11—11 of FIG. 8;

FIG. 12 is a partially diagrammatic side elevational view of a second embodiment of the invention;

FIG. 13 is a diagrammatic sectional view taken along line 13—13 of FIG. 12 of the second embodiment of the invention showing transducer placement.

DETAILED DESCRIPTION OF THE INVENTION

The embodiments of the invention illustrated and described herein are particularly adapted for testing the surface and shape of a mattress. While the following description of the invention will be related to this particular environment of mattress testing, it will be understood that the invention is not necessarily so limited, but might find other applications where it is desired to measure the contour or shape of a surface, particularly a deformable surface, with reference to the shape of the human body.

Figure 1:
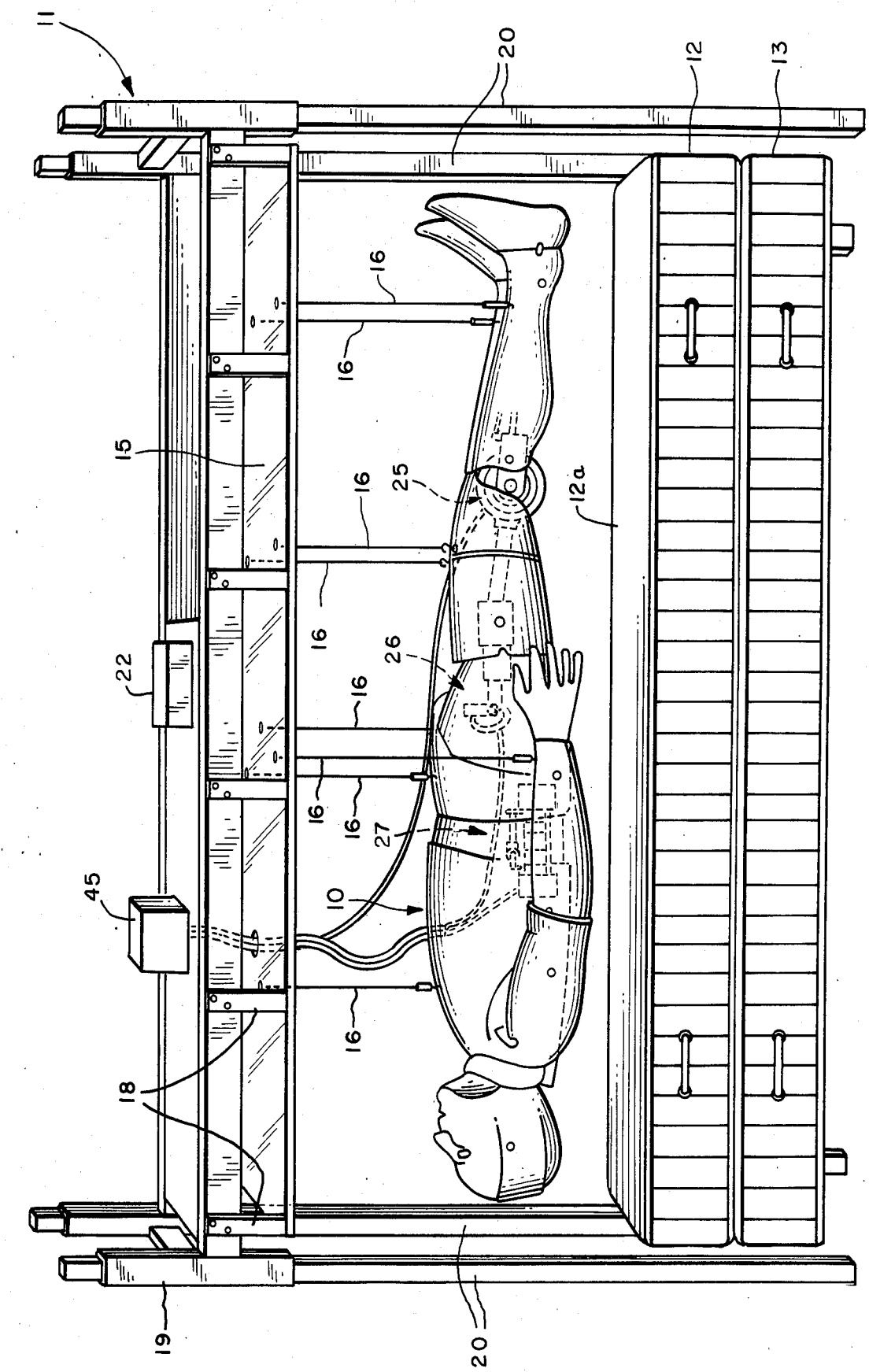
FIG. 1 is a side elevational view of a first embodiment of the invention.

With reference to FIG. 1, this embodiment of the invention is generally comprised of a humanoid FIG. 10 which is suspended in a supine (horizontal) position beneath a movable support assembly 11. The humanoid 10 is raised and lowered in relation to a mattress 12 supported on a box spring 13.

The humanoid 10 can be purchased from Humanoid Systems, 17022 Montanero St., Carson, Calif. 90746. it is a Model No. 572 dummy of a type commonly used in crash testing, for example, which has been modified in certain respects pertinent to this invention, as will be more fully described below.

The humanoid 10 is anthropomorphically "natural", reproducing the size, shape and weight of a human being of approximately 192 pounds. The unmodified humanoid 10 generally reproduces the movement of the major joints of the human body, e.g. ankle, knee, hip, torso, elbow, shoulder, neck. It also grossly reproduces areas of relative hardness and softness on the human body, as well as the mass distribution of the human body, including localized areas of higher or lower mass.

The humanoid 10 thus generally reproduces the shape, "feel" and relative mass distribution of the human body, as well as the range of movement of the major joints.

The humanoid 10 is suspended in a supine position (i.e., with its ventral side facing upwardly) from a plate 15, such as a thick plate of transparent acrylic plastic, which is part of the movable support assembly 11. A plurality of cables 16, such as common aircraft cables, are fixed at one end to the ventral side of the humanoid 10 at convenient points, with the other end of the cables 16 fixed to the plate 15, generally directly above their respective points of attachment on the humanoid 10.

The location points of the cables 16 on the humanoid FIG. 10 are not considered to be critical, but should be sufficient in number to maintain the humanoid FIG. 10 in a straight, relatively horizontal position when the humanoid is not resting on a surface. Some suitable mechanism permitting minor adjustments of cable length may also be used, such as an adjustable coupling mechanism. Flexible cables 16 are used which go slack when the humanoid 10 is resting with its full weight upon the mattress 12.

Plate 15 is connected by a plurality of brackets 18 to the underside of a support frame 19, which is mounted for movement along four vertically extending legs 20. A suitable drive mechanism schematically illustrated at 22 is used to drive the support frame 19 up and down the legs 20.

The entire movable support assembly 11 used in the illustrated embodiment is a modified common hospital bed Model No. 671 available from Joerns, 5555 Joerns Drive, Stephens Point, Wis. 54481. The plate 15 is installed on the Joerns bedframe, with the humanoid 10 thus suspended below the bedframe. Extended legs 20 were used with the bedframe for the necessary height. The drive mechanism 22 provided with the aforementioned Joerns hospital bed frame is utilized herein.

As previously set forth, this invention is useful in measuring the shape or contour of a surface as reflected in the deflection, or relative change in position, of various parts of a humman-like body. The humanoid 10 described herein has been particularly modified to make such a measurement of deflection in the area of the humanoid's knees (knee mechanism 25), hips (hip joint mechanism 26) and lower back/abdominal region, i.e., lower spine (spine mechanism 27). In this embodiment, deflection in a vertical plane, i.e., in a plane parallel to an imaginary plane bisecting the humanoid FIG. 10, is measured. No horizontal movements of the bodily parts of the figure are measured herein. Adaptation of the invention to measure such horizontal movements, as well as additional movements in a vertical plane other than those described herein, are of course within the broad concept of this invention.

Figure 2:
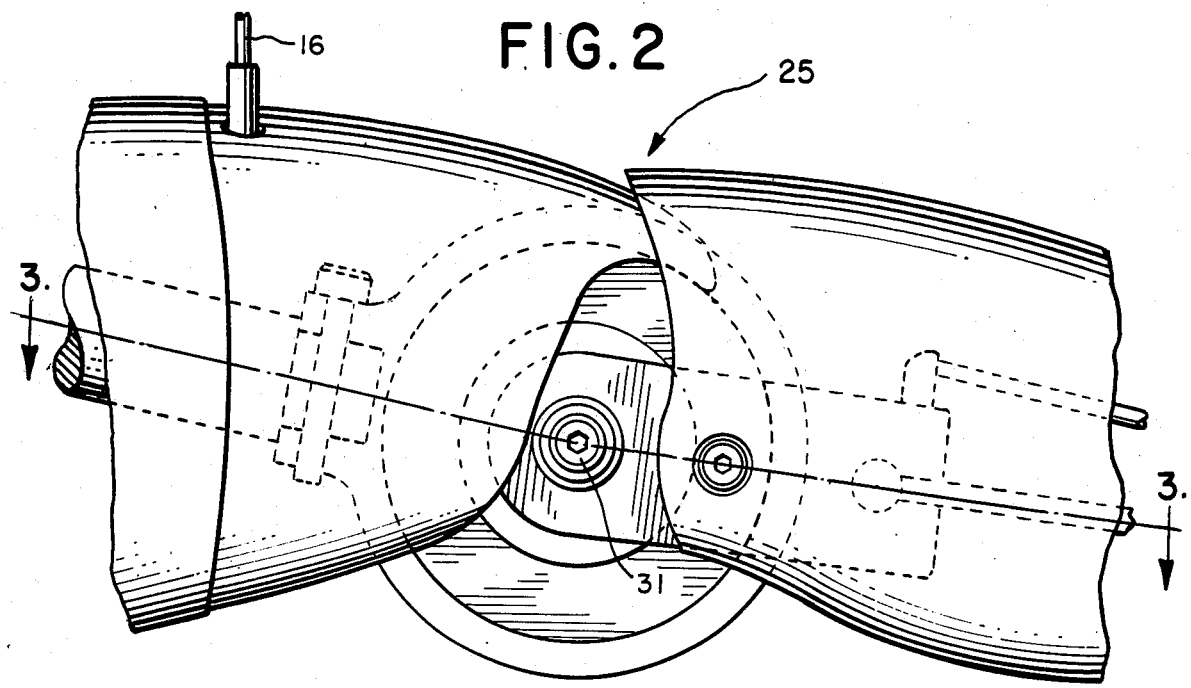
FIG. 2 is a view of the outboard side of the knee mechanism.
Figure 3:
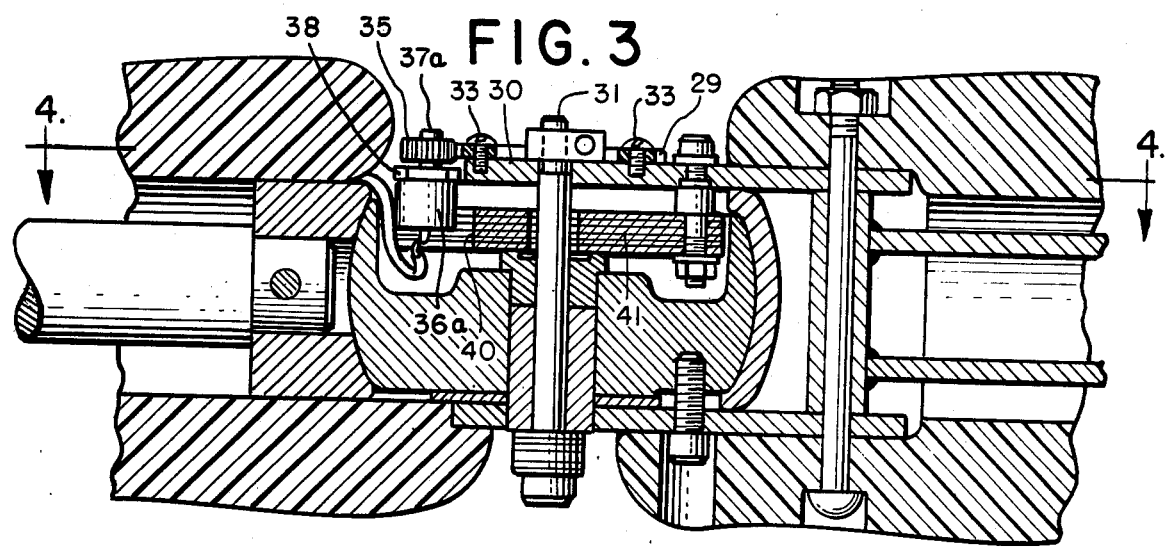
FIG. 3 is a sectional view of the knee mechanism taken along line 3—3 of FIG. 2.
Figure 4:
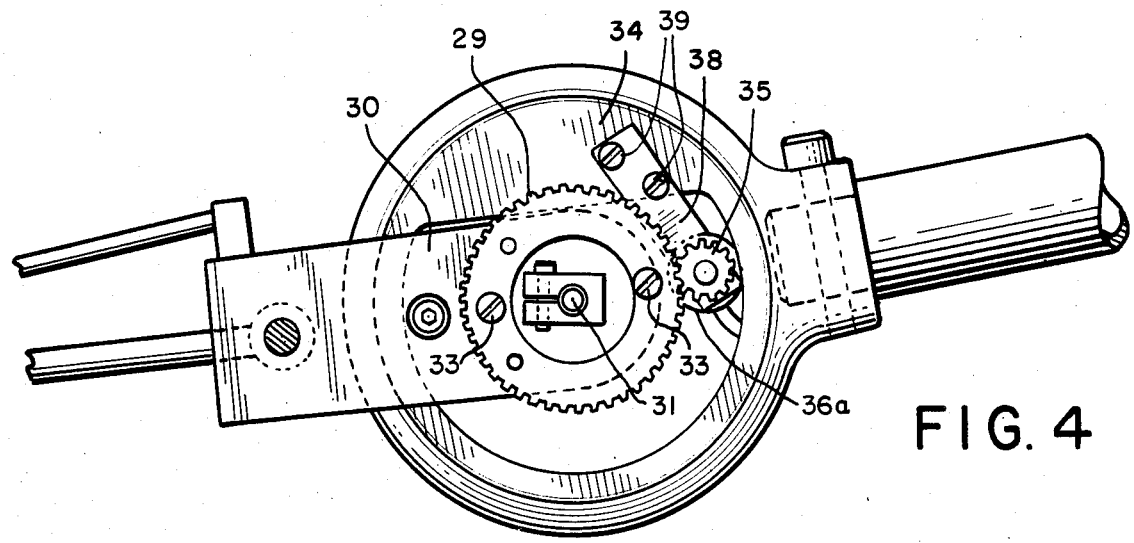
FIG. 4 is a sectional view taken along line 4—4 of FIG. 3 generally showing the inboard side of the knee mechanism.

The device for measuring the deflection of the knee is particularly shown in FIGS. 2-4. The knee mechanism of the aforementioned stock humanoid figure is modified through the addition of a large spur gear 29 which is fixed to a plate 30 on the inboard side of the knee concentric with a pivot pin 31 about which plate 30 pivots. As shown here, plate 30 and large spur gear 29 move with the lower leg. The spur gear 29 can be fuxed in position by any suitable means, as by screws 33.

Large spur gear 29 engages a much smaller spur gear 35 which is fixed to the stem 37a of a standard rotary potentiometer 36a, such as a Model 50-M125 rotary potentiometer available from Maurey Instruments, 4555 West 60th Street, Chicago, Ill. The rotary potentiometer 36a and associated small spur gear 35 are mounted on a bracket 38 which is fixed to a plate 34 forming part of the humanoid's general knee mechanism, as by screws 39. The plate 34 and bracket 39 move with the upper leg. It may be noted that a portion of the potentiometer 36a also extends through a bore 40 formed in a portion 41 making up the general knee mechanism of the stock humanoid. This bore 40 is simply an accommodation for the size of the potentiometer.

The potentiometer 36a, as well as the other potentiometers described hereinafter, are each connected in a circuit having a suitable power supply and voltage metering device (both schematically indicated at 45 in FIG. 1). Construction of the circuit is well within the ability of anyone of ordinary skill in the art, and it is simply designed to register changes in voltage in the circuit when the variable resistance of the rotary potentiometer is changed, as in the manner hereinafter described.

As previously noted, the large spur gear 29 is fixed to a portion of the humanoid's knee which rotates independently of the portion of the knee mechanism to which the small spur gear 35 and associated potentiometer 36a are mounted. Thus, as the knee mechanism 25 is deflected, such as when the humanoid 10 is placed on the surface 12a of the mattress, the aforedescribed portions of the knee move relative to one another, thereby causing the small spur gear 35 to be rotated, which in turn drives the potentiometer 36a. The change in voltage caused by this resistance change in the potentiometer is then detected at meter 45. That signal can then be translated into a measurement of deflection, i.e., vertical movement of the knee mechanism 25. Deflection of the knee is of course caused by the contour of the surface under the knee, thus yielding a measurement of surface contour which is directly related to positional changes caused in the knee mechanism 25. It may be additionally noted that by proper zeroing of the potentiometer 36a, deflection of the knee mechanism 25 upwardly as well as downwardly can be registered.

Both knee mechanisms 25 are identical, so only one need be described in detail herein. Likewise, only one hip mechanism 26 will be described in detail, since both are also identical.

Figure 5:
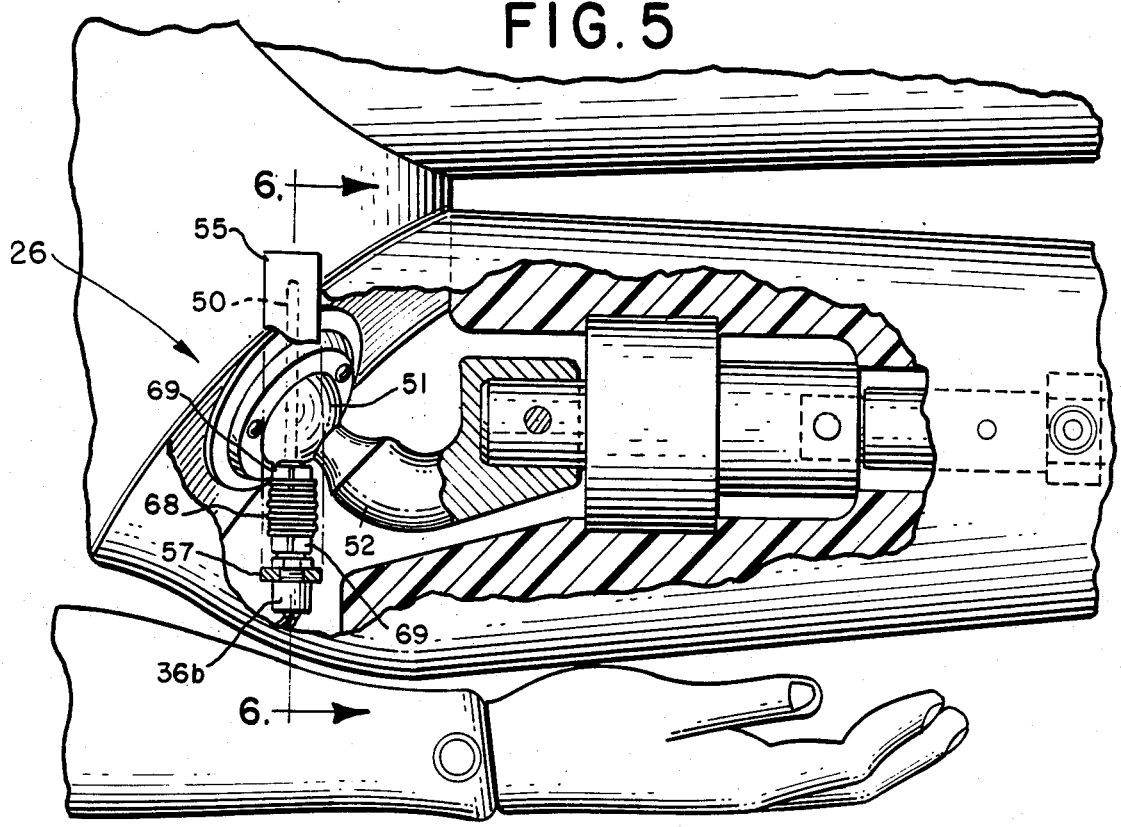
FIG. 5 is a plan view of the area of the hips, partly broken away for detail.
Figure 6:
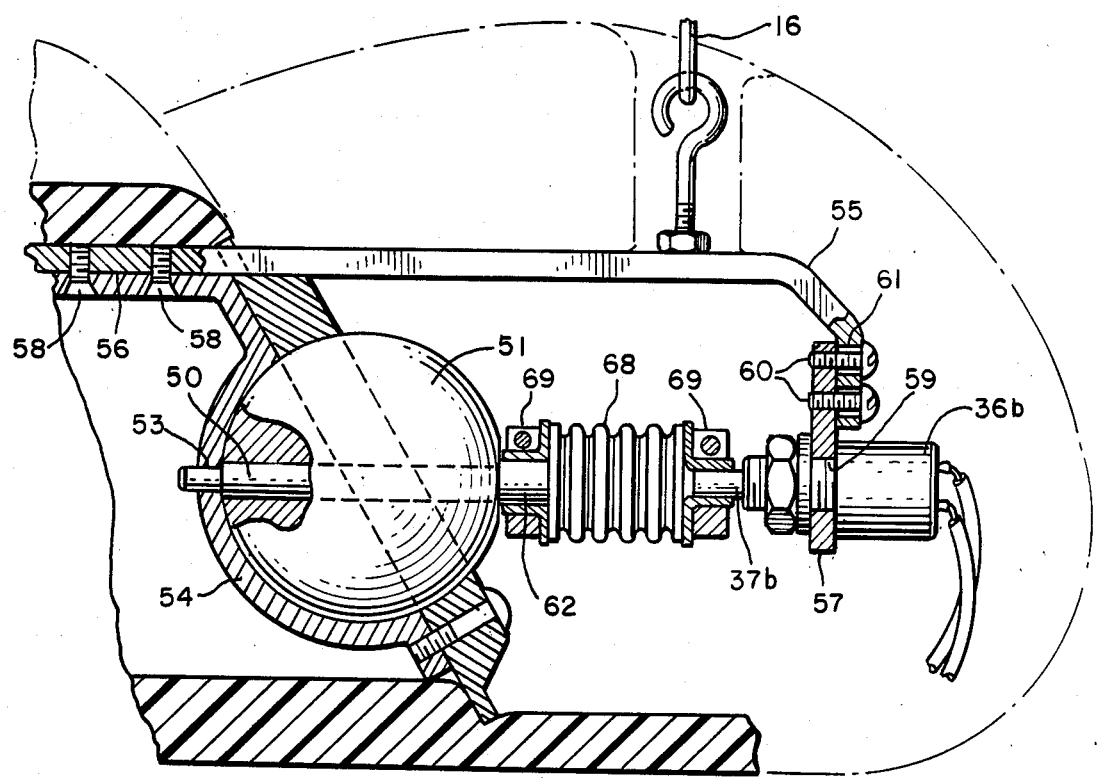
FIG. 6 is a sectional view taken along line 6—6 of FIG. 5 showing a hip joint mechanism.

The hip mechanism 26 of the humanoid 10 is illustrated in FIGS. 5 and 6. It is modified from the stock humanoid by inserting an elongated metal pin 50 through the approximate center of a ball portion 51 of a hip stem 52 along a line extending substantially perpendicular to the aforementioned imaginary vertical plane bisecting the humanoid 10. The pin 50 extends completely through the ball portion 51 and into a bore 53 formed in the metal pelvic portion 54 of the humanoid 10. The pin 50 is fixed within the ball portion 51, but is free to rotate in the bore 53. Pinning the hip stem 52 in this manner permits it to only rotate in a vertical plane, i.e., the normal three dimensional movement of this ball and socket joint is restricted to rotation about this pin 50.

An L-shaped bracket 55 is fixed at one end within a channel 56 formed in the metal of the pelvic portion 54 of the humanoid 10, as by screws 58. The other end of the bracket 55 extends downwardly, with a mounting plate 57 fixed thereto which carries another rotary potentiometer 36b. The potentiometer 36b is of the same type as potentiometer 36a.

Potentiometer 36b is mounted to extend through a hole 59 formed in the plate 57, with the potentiometer stem 37b extending inboard. The mounting plate 57 is attached to the bracket 55 by screws 60 which extend through associated bores 61 that are slightly elongated in the vertical direction. This provides some adjustability for the plate 57 to generally align the potentiometer stem 37b with the pin 50 to which the potentiometer 36b is connected in the following manner.

Pin 50 has a portion 62 which extends outboard from the ball portion 51 of the hip stem 52. The potentiometer stem 37b is connected to this portion 62 of the hip pin 50 by a tubular flexible connector 68. The ends of this connector 68 are respectively attached, as by clamps 69, to the potentiometer stem 37b and the hip pin portion 62. It will be noted that no particular significance is placed on the type of connector 68 used herein, but a flexible connector is deemed desirable to allow some leeway in alignment of the potentiometer stem and hip pin.

As previously noted, the hip pin 50 is fixed within the ball portion 51 of the hip stem 52, and therefore rotates with the ball portion 51. Rotation of the ball portion 51 thus rotates the potentiometer stem 37b via the connector 68, changing the potentiometer's resistance. The change in potential in the circuit in which potentiometer 36b is connected is then metered.

Rotary movement of the hip stem 37b results from movement of the upper leg relative to the pelvis. A measurement of surface contour beneath each of the hips, as reflected in this deflection, is thereby obtained. By proper zeroing of the potentiometer 36b, deflection of each of the hips upwardly as well as downwardly can be measured.

Relative movements of the lower torso and pelvis of the humanoid, i.e., in the area of the lower back/abdomen, is also detected and measured. The stock humanoid is modified to this end by the placement of a spine mechanism 27 in this area.

With reference to FIGS. 7-11, the spine mechanism 27 includes a spinal stack or column 75 which is composed of a plurality of "vertebra" in the form of intermediate discs 76a and end discs 76b. The discs 76a, 76b are formed from a rigid plastic material, such as Delrin, available from Dupont Corp. The discs 76a have generally hemispherically shaped hollows 78 formed on opposed sides of each intermediate disc 76a substantially concentric with the axis of each disc. Each end disc 76b has only one hemispherical hollow formed on the inboard side of the disc. The two discs 76b essentially serve as end caps for the spinal column 75.

A plurality of balls 79, such as steel ball bearings, are received in the opposed hemispherical hollows of adjacent discs 76a, 76b. Resilient ring spacers 82 made of a low durometer material, such as silicone rubber, are received in annular recesses 83 formed in the discs 76a, 76b substantially concentric with the disc axis. The recesses 83 are designed to oppose each other on assembly of the spinal column 75, such that a portion of a ring 82 is received and thereby carried within each of a pair of opposed recesses 83. The rings 82 are of a sufficient thickness such that adjacent discs 76a, 76b are spaced at least slightly apart upon assembly of the spinal column 75. The rings 82 provide a degree of resiliency to the column 75, and further serve to bias the discs 76a, 76b toward a straight stack configuration.

Spinal column 75 is completed by a cable 85 which extends along the longitudinal axis of the stacked discs 76a, 76b through a longitudinal channel 86 which extends through the discs and balls. Each end of the cable 85 is fixed in a bore 88 in a flange portion 87 formed on the outboard side of each disc 76b. It has been found advantageous herein to form screw threads about the cable ends and provide at least one threaded bore 88 in the flange portions 87 to thereby allow a disc 76b to be rotated to adjust the compression of the spinal column 75.

It will thus be seen that a spinal column 75 is provided which is similar in construction and movement to a portion of the human spine.

The spinal column 75 is mounted between an upper spine support assembly 95 and a lower spine support assembly 96. Upper spine support assembly 95 has a spine support mount 97 which is mounted to the inboard side (i.e., side facing the sprinal column 75) of an end cap 98, as by screws (not shown). The end cap 98 is in turn fixed in a suitable fashion within one end of a cavity 101 provided in the humanoid 10.

Either flange portion 87 on one end of the spinal column 75 is received in an elongated horizontal recess or slot 105 formed in the inboard side of the upper spine mount 97. Flange portion 87 is releasably retained in place through the use of set screws 106 extending through a pair of threaded bores 107 and received in suitable detents 89 formed in each flange portion 87 (best shown with reference to FIG. 10).

The flange portion 87 of the other end of the spinal column 75 is likewise received in an elongated recess or slot 108 formed in the inboard side of a lower spine mount 109. A like pair of set screws 106 extend through threaded bores 107 in the lower spinal mount 109, and are received in detents 89 formed in the flange portion 87.

Lower spine mount 109 is fixed to the inboard side of a lower end cap 110, as by screws 111. Lower end cap 110 is in turn fixed in a suitable fashion within the other end of the cavity 101 provided in the humanoid 10. It must be noted that spinal column 75 serves to interconnect the torso of the humanoid 10 with its pelvic area. The humanoid 10 is otherwise freely movable in this region.

A sensor is provided to measure relative vertical movement or shear of the upper and lower spine assemblies 95, 96. With specific reference to FIGS. 7 and 8, a bracket 99 is fixed at one end to the lower end cap 110. The other end of the bracket 99 is free and is located adjacent upper end cap 98. A potentiometer 36e is mounted to the free end of bracket 99, and has a lever arm 100 extending radially from its stem 37e. Lever arm 100 is pivotally connected to a link 102, which in turn is connected to the upwardly facing side of upper end cap 98.

It will thus be seen that relative vertical movement of the upper and lower spine assemblies, i.e., one spine assembly moving upwardly or downwardly relative to the other, will cause lever arm 100 to turn. This rotates the potentiometer stem 37e causing a voltage change (due to the change in the potentiometer's resistance) in the circuit in which potentiometer 36e is connected. This voltage change can then be correlated to the relative vertical displacement between the spine support assemblies 95, 96.

A pair of relatively flexible wires 115a and 115b extend generally parallel to the spinal column 75, with wire 115a located upwardly from the spinal column, and wire 115b located beneath the spinal column (as the spinal column 75 is viewed in FIG. 1, for example). The two wires 115a, 115b are in the same generally vertical plane, i.e., the imaginary vertical plane bisecting the humanoid 10.

Wire 115a is fixed at one end in the upper spine mount 97. Here, this end of wire 115a is swaged, with the swaged end received in a well 117a having a bore 118a through which wire 115a extends. The other end of wire 115a extends through a bore 116a which passes through lower spine mount 109 and into a cavity 120 within the lower end cap 110. Similarly, lower wire 115b is fixed to upper spine mount 97, having its swaged end received in a well 117b having a bore 118b, and extends through a bore 116b through the lower spine mount 109 and into the cavity 120.

With particular reference to FIG. 11, a pair of rotary potentiometers 36c and 36d (both similar to potentiometer 36a) are mounted to a housing 119 fixed within the end cap 110. Rotary potentiometer 36c has a lever arm 121 which is fixed to its potentiometer stem 37c and extends radially therefrom. The lever arm 121 has a lug 122 on its unfixed end to which the upper cable 115a is attached. Potentiometer 36d, in a similar fashion, has a lever arm 123 fixed to its potentiometer stem 37d, with a lug 125 located on its unfixed end to which the lower wire 115b is attached. A spring 126 is connected between each of the lever arms 121, 123 and on outboard spring mount 127 fixed within end cap 110. The springs 126 serve to bias the lever arms 121, 123 to a "start" or zero position. The operation of the spine mechanism 27 to reflect relative spinal movement between the torso and pelvis, i.e., deflection in the abdominal area, can now be described.

When the abdominal region of the humanoid 10 is deflected upwardly or downwardly, the spinal column 75 will bend in a like manner. This permits the upper and lower spine support assemblies 95, 96 to pivot or cant upwardly or downwardly in relation to the movement of the spinal column 75. This canting in turn pulls one of the wires 115a, 115b against the spring bias. The other wire conversely yields to its spring bias, i.e., is pulled toward the end wall to which the spring is attached. The wire 115a, 115b placed under additional tension (pulled against the spring bias) causes the lever arm 121, 123 to which it is connected to be pulled toward the spinal column 75, thereby rotating the stem 37c, 37d of the associated potentiometer 36c, 36d resulting in a change of resistance therein. In a similar manner, the wire 115a, 115b under reduced tension (yielding to the spring bias) has its lever arm 121, 123 pulled away from the spinal column 75, thereby resulting in a change in resistance of its associated potentiometer 36c, 36d. Both potentiometers 36c and 36d are connected in a suitable circuit with power supply and metering device 45 in a manner similar to potentiometer 36a, such that a change in resistance of potentiometer 36c or 36d causes a voltage change which reflects the amount of deflection of the "spine" of the humanoid 10.

By way of illustrative example, if the abdomen of the humanoid FIG. 10 is deflected downwardly, upper wire 115a of the spinal assembly 27 would be under less tension while lower wire 115b would be placed under greater tension. Wire 115b would thereby cause lever arm 123 to be pulled toward the spinal column 75.

Movement of the lever arm 123 rotates the stem portion 37d of the potentiometer 36d to which it is fixed. In a similar fashion, lever arm 121 would be pulled by its spring 126 away from spinal column 75, rotating stem portion 37c of potentiometer 36c. The voltage changes produced in the circuit can then be translated into a measurement of the amount of downward deflection of the spinal assembly 27. This downward deflection of course relates to the contour of the surface beneath this area of the humanoid 10, thus yielding a measurement of the deformed humanoid configuration, and hence the surface shape in this region.

In operating the foregoing embodiment of the invention, each of the various potentiometers are zeroed to establish a base line for the humanoid 10 in a rest position, i.e., suspended in a relatively straightened supine position from the movable support assembly 11. The drive motor 22 of the movable support 11 is then actuated to lower the humanoid 10 onto surface 12a of the mattress 12. Lowering stops approximately at the point where the suspension cables 16 go slack, with the entire weight of the humanoid 10 then supported by the mattress 12. Depending on the contour of the mattress surface 12a under the wide area load imposed by the humanoid 10, various portions of the humanoid's body will move relative to one another. This relative movement, or vertical deflection, is registered in the areas of the knees, hips and lower back/abdomen by the respective potentiometers located in these areas. Since the deflection of these areas is related to the surface contour of the mattress 12, a measurement of the mattress contour is thus obtained.

A second embodiment of the invention is shown in FIGS. 12 and 13. It will be understood that numbers in common between this embodiment and the foregoing embodiment designate substantially the same part or portion.

In this second embodiment, the humanoid 10 is substantially unmodified from the stock figure obtainable from the aforementioned source. That is, no modification of the knees, hips or "spine" is made as described in the previous embodiment. Instead, a plurality of linear transducer mechanisms 140a-140j, such as Model PT-101-15A linear transducers available from Celesco Company Transducer Products, Inc., Canoga Park, Calif., are utilized to register relative movement of the body parts of the humanoid.

Each linear transducer 140a-140j has a respective cable portion 141a-141j which is connected by a suitable connector 142 at a point on the ventral side of the humanoid 10. Here, transducer connector points are located at the ankles, knees, hips, lower and upper abdomen, and on both sides of the upper torso.

Each of the linear transducers 140a-140j is located generally directly over its respective attachment point and is mounted to the lower portion of the plate 15. While any number of linear transducers can be used in this embodiment, depending on the number of data points desired, the ten transducers illustrated herein attached at the points described are presently deemed to be optimal.

The linear transducers 140a-140j are each connected in a circuit having a suitable power supply and voltage metering device (both schematically indicated at 145 in FIG. 12). Construction of a circuit to register voltage changes caused by resistance changes in the linear transducers is well within the ability of anyone of ordinary skill in the art.

In operation of this embodiment, the humanoid 10 is lowered onto a rigid surface, such as a board, laid across the mattress surface 12a. The various transducers 140a-140j are then zeroed to this baseline position. The humanoid is then raised, the board removed, and then lowered again until it comes to rest on the surface 12a of mattress 12. Lowering stops when the suspension cables 16 go slack, with the full weight of the humanoid 10 thereby supported on the mattress surface 12a.

Movement of the various bodily parts of the humanoid 10 from the zero position, caused by settling into the mattress surface 12a and conforming to its shape and contour, will deflect the bodily parts in a manner which is registered by the associated transducers 140a-140j. Since each such deflection is caused by the contour of the mattress below the particular body part, a measurement of the shape or contour of the mattress under the wide area load of the humanoid is obtained.

Such a measurement of mattress contour is of particular utility in designing improved mattresses. For example, measurements made using this invention could indicate areas of a given mattress design which require adjustment to either increase or decrease the "firmness" in such areas, as by a change in spring arrangement, spring compression, covering material, and the like.

Thus, while this invention has been described in regard to two particular embodiments, those possessing skill in this art will recognize modifications and equivalents of the invention which fall within in the scope of the following claims.

What is claimed is:

1. Apparatus for use in measuring the contour of a surface of an article adapted to support the human body, comprising, a humanoid figure having bodily segments including a pair of legs and a pair of hips, each of said legs being connected together and movable at a knee joint and at a hip joint in a manner similar to the movement of two comparable human body segments, and means for separately detecting the relative movement of said leg segments at each of said knees and at each of said hip joints when said humanoid is located on a surface to thereby obtain a measurement of surface contour when under load from the humanoid.

2. The apparatus of claim 1 wherein some of said bodily segments define an upper and a lower back, and further including spine means for connecting said upper and lower back segments, said means for detecting relative movement including separate means for detecting relative movement of said upper and lower back segments at said spine means.

3. The apparatus of claim 2 wherein said spine means comprises a plurality of discs arranged in a stack, adjacent discs in said stack having opposed hemispherical hollows formed therein defining a plurality of cavities in said stack, a ball received in each of said cavities about which opposed discs can slide, a plurality of resilient spacers each separating adjacent discs in said stack, a semi-flexible cable interconnecting said discs, balls and resilient spacers into said stack and permitting radial flexion of said stack, said cable being fixed at each of its ends to prevent said stack from coming apart, and means for mounting said stack between said upper and lower back segments.

4. The apparatus of claim 3 wherein said means for detecting relative movement of said upper and lower back segments at said spine means comprises a first flexible wire carried at one of its ends by one of said upper and lower back segments, said first wire extending generally parallel to said spine stack when said stack is in an unflexed condition, the other end of said first wire being connected to a first lever arm fixed to a first rotary potentiometer, said rotary potentiometer being carried by the other of said upper and lower back segments, and a second flexible wire carried at one of its ends by one of said upper and lower back segments, said second wire extending generally parallel to said spine stack when said stack is in an unflexed condition, the other end of said second wire being connected to a second lever arm fixed to a second rotary potentiometer carried by the other of said upper and lower back segments, and means for biasing said lever arms to a zero position, said first and second flexible wires being located on opposite lateral sides of said stack and in an imaginary plane generally bisecting said humanoid, whereby bending movement of said stack in said imaginary plane causes one or the other of said first and second flexible wires to go into tension thereby pulling its associated lever arm and driving its associated potentiometer.

5. The apparatus of claim 1 wherein said separate means for detecting relative movement at each of said knees comprises a first gear fixed to one of a lower leg segment and an upper leg segment which meshes with a second gear rotatably carried on the other of said upper leg segment and lower leg segment, said upper and lower leg segments pivoting at said knee, and a first rotary potentiometer driven by rotary movement of said second gear.

6. The apparatus of claim 5 wherein said separate means for detecting relative movement at each of said hip joints comprises a second rotary potentiometer, a mount for supporting said second rotary potentiometer adjacent a hip ball formed on said upper leg segment, and connector means for connecting said second rotary potentiometer to said leg at said hip ball such that said second rotary potentiometer is driven by rotary movement of said hip ball.

7. Apparatus for use in measuring the contour of a surface of an article adapted to support the human body, comprising,
a humanoid figure having bodily segments defining legs having knee joints, hips having hip joints with said legs, and a torso connected to said hips, said bodily segments being movable in a manner similar to the movement of comparable human body segments, and
means for detecting the relative movement of said bodily segments comprising a plurality of linear transducers connected at points on said humanoid to detect movement of said bodily segments about said knee joints, said hip joints, and of said torso relative to said hip joints when said humanoid is located on a surface to thereby obtain a measurement of surface contour when under load from the humanoid.

8. Apparatus for use in measuring the contour of a deformable surface adapted to support the human body, comprising:
a humanoid figure having bodily parts including legs having knee joints, hips having hip joints with said legs, and a mid-section, all of said bodily parts generally comparable in size, exterior shape, movement and weight to those of a human being,
means for registering the relative movement of said bodily parts in the area of said knees, said hip joints and said mid-section, and
means for placing said humanoid on a surface to be tested.

9. The apparatus of claim 8 wherein said means for placing said humanoid on the surface is a vertically movable frame, said humanoid being suspended by flexible cables beneath said frame in a supine position, and wherein said means for registering the relative movement of said bodily parts comprises a plurality of linear transducers, each of said transducers having a cable attached to a point on said humanoid and being mounted on said frame.

10. The apparatus of claim 8 wherein the deformable support surface being measured is a mattress.

11. An apparatus for use in measuring the deformed profile of a human-shaped object in relation to a surface adapted to support the human body comprising:
a humanoid figure having bodily parts including legs having knee joints, hips having hip joints with said legs, and a mid-section, all of said bodily parts generally comparable in size, exterior shape, movement and weight to those of a human being,
means for registering the relative movement of said bodily parts in the area of said knees, said hip joints and said mid-section, and
means for placing said humanoid on a surface to be tested.

* * * * *